100
United States Patent [19]

Mullin et al.

[11] Patent Number: 4,599,150

[45] Date of Patent: Jul. 8, 1986

[54] PREPARATION OF ADDUCTS

[75] Inventors: John B. Mullin, West Malvern; Arthur K. Holliday, Bromborough; David J. Cole-Hamilton, Ormskirk; Anthony C. Jones, St. Helens; Neil D. Gerrard, Liverpool, all of England

[73] Assignee: The Secretary of State for Defence in Her Britannic Majesty's Government of the United Kingdom of Great Britain and Northern Ireland, London, England

[21] Appl. No.: 668,686

[22] Filed: Nov. 6, 1984

Related U.S. Application Data

[63] Continuation of Ser. No. 521,828, Aug. 10, 1983, abandoned.

[30] Foreign Application Priority Data

Aug. 13, 1982 [GB] United Kingdom ................. 8223418
Feb. 24, 1983 [GB] United Kingdom ................. 8305166

[51] Int. Cl.$^4$ .............................................. C25B 1/00
[52] U.S. Cl. ............................................ 204/59 QM
[58] Field of Search ................................. 204/59 QM

[56] References Cited

U.S. PATENT DOCUMENTS 3,164,538  1/1965  Ziegler et al. ...................... 204/59
3,391,066  7/1968  Baithwaite ....................... 204/59 QM

FOREIGN PATENT DOCUMENTS 0080844  6/1983  European Pat. Off. .

OTHER PUBLICATIONS

"Chemical Abstracts", vol. 93, No. 6, Synthetic High Polymers, Fred W. Billmeyer, Aug. 11, 1980.
"Chemical Abstracts", vol. 81, No. 14, Synthetic High Polymers, Fred W. Billmeyer, Oct. 7, 1974.

*Primary Examiner*—R. L. Andrews
*Attorney, Agent, or Firm*—Cushman, Darby & Cushman

[57] ABSTRACT

A method of producing an adduct of an organometallic compound $M(R^1)_3$ where M is either indium or gallium and $(R^1)_3$ represents a plurality of organic radicals which may be the same or different, preferably methyl or ethyl groups, comprising electrolysing, using a sacrificial anode of the metal M, a solution containing components 1 and 2 as follows:

component 1: one or more organomagnesium halide compounds $R^1MgX$ where X is a halide radical selected from Cl, Br and I; where $R^1$ represents one of the groups contained in $(R^1)_3$;

component 2: a polar aprotic liquid which is a solvent for component 1, e.g. tetrahydrofuran, diethyl ether, di-isopentyl ether, di-n-butyl ether, diphenyl ether or anisole.

Preferably, the solution electrolysed additionally contains a third component, component 3, which is one or more organic halides $R^1X_4$, where $R^1$ is one of the groups contained in $(R^1)_3$, $X_4$ is a halide radical preferably the same as X, the polar aprotic liquid being a solvent also for component 3.

13 Claims, No Drawings

PREPARATION OF ADDUCTS

This is a continuation of application of Ser. No. 521,828, filed Aug. 10, 1983, now abandoned.

The present invention relates to the preparation of adducts which may be used in the preparation of compound semiconductor materials.

Compound semiconductor materials, e.g. materials such as gallium arsenide, indium phosphide, gallium phosphide and cadmium mercury telluride, are well known materials having uses in the electronics industry in such applications as microwave oscillators, semiconductor light emitting diodes and lasers, and infrared detectors.

Such materials have been made in the past by forming, usually on a substrate crystal, one or more active layers, by the method of vapour phase epitaxy (VPE).

It has been known for some time to produce VPE compound semiconductors of the form $M^A Q^A$ where $M^A$ is Group III element and $Q^A$ is Group V element by reacting a trialkyl of the element $M^A$ with a gaseous compound, eg a hydride, of the Group V element $Q^A$. This method is a suitable method of preparing gallium arsenide from $Ga(CH_3)_3$ and $AsH_3$ for example.

The present invention provides a novel process suitable for the preparation of the trialkyls of the Group III metals $M^A$.

In the case where $M^A$ is In and $Q^A$ is P, unwanted involatile polymers are formed in the reaction of $In(CH_3)_3$ and $PH_3$ and this problem has led to research into alternative methods of preparing the III-V semiconductor compounds.

More recently, an approach has been used in the preparation of III-V compounds which in the case of indium phosphide avoids the formation of unwanted polymers. Adducts (coordination complexes) of trialkyl compounds of both $M^A$ and $Q^A$, i.e. adducts of the form $M^A(R^A)_x.Q^A(R^B)_x$, where $R^A$ and $R^B$ are metal alkyls (where x=3), have been formed, e.g. $(CH_3)_3In.P(C_2H_5)_3$ and $(CH_3)_3In.N(C_2H_5)_3$. These adducts provide a favourable route to the required semiconductor materials because (i) they are very stable in an inert, water-free atmosphere; (ii) they may be easily purified by sublimation or zone refining; and (iii) they may be decomposed pyrolytically at normal pressure to give the required semiconductor material either alone or in the presence of a group V hydride.

In a copending UK Patent Application No. 8233121 by the present Applicant there is described a novel method of preparing an adduct suitable for conversion into a compound semiconductor of a Formula $M^1(R^1)_x.(Q(R^2)_y)_z$ where $M^1$ is a Group II or Group III metallic element, Q is a Group V or Group VI element which is able to combine with $M^1$ to form the required compound semiconductor, x is an integer equal to the valency of $M^1$, y is an integer equal to the valency of Q, z is an integer equal to 1 or 2 and $(R^1)_x$ and $(R^2)_y$ each represents a plurality of organic radicals which are the same or different radicals, which method is characterised in that a precursor adduct of the form $M^1(R^1)_x.L$ is reacted with a compound $Q(R^2)_y$, the precursor adduct being less stable than the required adduct suitable for conversion into the compound semiconductor, L being a radical which is more volatile (and usually less electron donating) than $Q(R^2)_y$. If x=3, y=3 and z=1. If x=2, z=1 or 2 and yz=2.

The present invention also provides a method of preparation suitable for production of an adduct which may be used as the precursor adduct.

In copending UK Patent Application No. 8233121 also by the present Applicant there is described a method of producing an adduct of an organometallic compound $M^1(R^1)_x$, where $M^1$ is a Group II or Group III metallic element and $(R^1)_x$ represents a plurality of organic radicals, e.g. alkyl groups, which may be the same or different, x being an integer equal to the valency of $M^1$, which method comprises electrolysing, using a sacrificial anode of the metal $M^1$, a solution containing components A, B and C as follows:

A: an organometallic compound $M^2(R^1)_v$ where $M^2$ is a metallic element of valency v;

B: a readily ionisable support electrolyte providing relatively large anions and cations, e.g. tetraethylammonium perchlorate;

C: a polar aprotic liquid which is a solvent for both components A and B, preferably tetrahydrofuran; the metal $M^1$ being selected from the group consisting of: indium, gallium and cadmium and the metal $M^2$ being a metal more electropositive than $M^1$, $M^2$ being preferably magnesium.

The method of adduct preparation described in UK Patent Application No. 8233120 has proved satisfactory but has certain disadvantages. Firstly, the support electrolyte component B is required and this is not an inexpensive component. It may have to be replaced from time to time owing to breakdown during use. Secondly, only very low currents may be used and this means that very long reaction times are required in order to obtain useful quantities of the product. Thirdly, where $M^1$ is indium and $M^2$ is Mg, Mg is deposited at the cathode initially as required; however, later in the electrolysis, indium starts to be deposited and a steady state develops when no more of the adduct is produced. This means that the yield obtained is low. Fourthly, where $M^2$ is magnesium and $R^1$ is methyl the compound $R^1{}_2Mg$ has to be isolated and purified in a separate vessel before transfer to the electrolysis apparatus.

It is one object of the present invention to provide an improved method of adduct preparation which does not have the disadvantages mentioned above.

It is another object of the present invention to provide a method of preparation of adducts suitable for conversion into radical free metal trialkyls $M^A(R^1)_3$.

According to the present invention there is provided a method of producing an adduct of an organometallic compound $M(R^1)_3$ where M is either indium or gallium and $(R^1)_3$ represents a plurality of organic radicals which may be the same or different, comprising electrolysing, using a sacrificial anode of the metal M, a solution containing components 1 and 2 as follows;

component 1: one or more organomagnesium halide compounds $R^1MgX$ where X is a halide radical selected from Cl, Br and I; where $R^1$ represents one of the groups contained in $(R^1)_3$;

component 2: a polar aprotic liquid which is a solvent for component 1.

Preferably, the solution electrolysed also contains a third component, component 3, which is one or more organic halides $R^1X_A$, where $R^1$ is one of the groups contained in $(R^1)_3$, $X_A$ is a halide radical preferably the same as X. Component 3 is preferably in excess.

In the case where component 3 is used the polar aprotic liquid, component 2, is also a solvent for component 3.

Component 3 is not strictly essential for the success of the reaction but increases the yield of the adduct relative to that of Mg. As Mg deposits at the cathode it redissolves to give more organomagnesium halide in the presence of the excess organic halide $R^1X_A$.

In the method according to the present invention the groups $R^1$ may for instance be optionally substituted alkyl or aryl radicals.

The groups $R^1$ are preferably alkyl groups having from 1 to 7 carbon atoms, particularly ethyl or methyl.

Preferably, the groups $R^1$ are the same groups.

Preferably, the compound $R^1MgX$ where X is preferably iodide or chloride and $R^1$ is preferably methyl or ethyl, is obtained in a pure form by the addition of excess $R^1X$ to a suspension of magnesium in an ethereal solvent.

Preferably component 3 is methyl chloride or methyl iodide.

Preferably, the concentration of component 1 in component 2 is between 0.01 and 5 mole/liter, desirably between 0.1 and 2 mole/liter.

The polar aprotic liquid, component 2, may be selected from the following solvents (or mixtures thereof): tetrahydrofuran, dioxan, N-methyl pyrollidone, diethyl ether, di-n-propyl ether, di-n-butyl ether, di-n-pentyl ether, di-isopentylether, acetonitrile, nitromethane, propylene carbonate, diphenyl ether and phenyl alkyl ethers, e.g. anisole, having from 1 to 7 carbon atoms in the alkyl group.

Where the adduct formed by the method according to the present invention is to be used as a precursor adduct for conversion into a more stable adduct suitable for decomposition into a compound semiconductor by the method described in UK Patent Application No. 8233121, the precursor adduct is preferably formed using tetrahydrofuran (thf) as the polar aprotic liquid, the adduct preferably being a 1:1 adduct of thf and a trialkyl indium or gallium, particularly a trialkyl indium.

As noted above adducts of compounds $M^1(R^1)_x$ which are adducts of the form $M^1(R^1)_x.Q^1(R^3)_x$ are known and may be preferred to the basic compounds $M^1(R^1)_x$ for decomposition into the compound semiconductors $M^1Q^1$. However, these adducts have been prepared hitherto directly from the basic compounds $M^1(R^1)_x$ which, as noted above, are themselves expensive and difficult to prepare, and can also be relatively dangerous. As noted above, the method described in copending Application No. 8233121 provides a route to these adducts from precursor adducts of the form $M^1(R^1)_x.L$ where L is a radical more volatile (and usually less electron donating) than $Q^1(R^3)_x$ thus allowing use of the compounds $M^1(R^1)_x.L$ to be avoided is appropriate.

The present invention unexpectedly provides a method of preparing the precursor adducts $M^1(R^1)_x.L$ wherein $M^1$ is In or Ga and x is 3 which avoids intermediate use of the compounds $M^1(R^1)_x$ and which can be simpler and cheaper than methods used for preparation of the compounds $M^1(R^1)_x$. In addition, the method according to the present invention does not have the disadvantages shown by that of UK Patent Application No. 8233120 in that no support electrolyte is required, higher yields are possible using a greater electrolysis currents and the starting Grignard reagent may be prepared in the vessel used for the subsequent electrolysis.

Electrolytic methods involving the use of Grignard reagents have previously been used to prepare organometallic compounds. However, such methods have been aimed at the direct preparation of metal alkyls per se (the free radical metal alkyls), such as lead tetraethyl. They have not previously been aimed at the preparation of adducts, and adducts of gallium and indium compounds, e.g. alkyls, in particular have consequently never been made by such methods. However, as noted above, it may be desirable to avoid the formation and use of metal alkyls per se in the preparation of semiconductor compounds containing the metals, e.g. Ga and In. It is surprising therefore that the direct production of these metal alkyls per se can, if appropriate, be avoided by the method according to the present invention, which yields the desired adducts instead.

Certain adducts of metal alkyls have also been prepared previously by non-electrolytic methods using Grignard reagents. However, the electrolytic method according to the present invention is superior to such methods. For example, $Me_3Ga.Et_2O$ (Me=methyl Et=ethyl) has previously been prepared by Grignard alkylation of $GaCl_3$. However, the $GaCl_3$ is air-sensitive, and requires prior synthesis and this adds an extra production step to the process. $Me_3In.Et_2O$ has previously been prepared in a similar way and in this case the indium chloride is not as easily handleable as the indium wire which may be used in the method of the present invention.

Although, as noted above, it may in some circumstances be desirable to avoid the use of metal alkyls per se, e.g. trimethyl indium, in the preparation of semiconductor compounds, it may nevertheless be appropriate to prepare such radical free compounds if required. For example, such compounds may be specially required for use in an existing process and/or to give a high purity semiconductor product. In that case, it has been found that adducts prepared by the method according to the present invention may be converted into the required radical free metal alkyl by further steps providing a suitable conversion route.

As a first example, the adduct $In(CH_3)_3.Et_2O$, where Et=ethyl, may be converted into free $In(CH_3)_3$ by distillation following the addition of benzene.

As a second example, the adduct $Ga(CH_3)_3.Ip_2O$ where Ip=isopentyl (3,3-dimethylpropyl) may be formed and converted into radical-free $Ga(CH_3)_3$ by fractional distillation above the decomposition temperature of the adduct in the manner described in copending UK Patent Application No. 8218820 by the present Applicant and reproduced below in Descriptive Examples A and B.

As a third example, the adduct $Ga(CH_3).Et_2O$ may be used to form $Ga(CH_3)_3.Ip_2O$, followed by removal of volatile impurities by evacuation and then dissociating the adduct by heating above its decomposition temperature and fractionating the resultant mixture as described in UK Patent Application No. 8218820 and reproduced below to Descriptive Examples A and B.

In general terms, where it is desired to produce a radical free trialkyl of gallium, the following preparation process is preferably used.

Step 1:

An adduct of the trialkyl gallium and one of the solvents listed above which is an ether is formed by the electrolytic method according to the present invention using the appropriate ether radical as the polar aprotic liquid, component 2, and the appropriate Grignard reagent to give the trialkyl group. Where the ether itself has a boiling point 50° C. or more, preferably 100° C. or more, higher than the boiling point of the trialkyl gallium, the adduct may be used directly in Step 3. Where the ether has a boiling point which is not 50° C. or more higher than the boiling point of the trialkyl gallium the adduct is first used in Step 2.

Step 2:

If the ether is relatively volatile, i.e. has a boiling point which is not 50° C. above that of the trialkyl gallium, the ether radical of the adduct is replaced by a less volatile ether radical as specified above, for use in Step 3 by adding the appropriate less volatile ether (preferably in excess) to the adduct to give a radical exchange.

Step 3:

The resultant adduct from Step 1 or Step 2 as appropriate is treated so as to remove volatile impurities, preferably by evacuation, e.g. at ambient temperature, or by heating at a temperature of between 20° C. and 120° C. below the adduct decomposition temperature.

Step 4:

The adduct purified as in Step 3 is then heated at a temperature at which it dissociates to form the radical free trialkyl gallium. This is separated by fractional distillation as described in UK Patent Application No. 8218820.

Since the electrolytic Grignard method according to the present invention does not directly yield radical-free gallium and indium organometallic compounds, e.g. alkyls, it appears at first sight not to be an attractive method to use where such radical-free compounds are sought. However, we have found, for example, that if the overall process involving Steps 1 to 4 (or 1, 3 and 4 where appropriate) is used as a route to the radical-free trimethyl gallium this compound may conveniently be obtained with an extremely high purity. Trimethyl gallium, when prepared using conventional routes, normally requires, in any event, additional treatments to obtain the appropriate level of purity. Thus, the process can, in fact, afford a valuable route to the radical free compound if required (as well as to the precursor adduct and adducts formed therefrom if alternatively required).

Embodiments of the present invention are described by way of example in some of the following Examples.

In the following Examples, Examples 1 and 2 are examples of the preliminary preparation of methylmagnesium halides used in certain subsequent Examples, Examples 3 to 6 and 11, 12, 14 and 15 are examples of methods embodying the present invention and Examples 8 to 10, 13 and 18 to 22 are examples of methods of using the products of methods embodying the invention.

In the following Examples all chemicals and solvents used were previously dried and purified by standard methods. All electrochemical preparations were carried out in an atmosphere of dry oxygen-free nitrogen using a three-necked flask fitted with a water condenser, platinum cathode and an indium or gallium anode. The power supply was a Solarton Vari-Pack, Model SRS 153 (Trade Mark).

EXAMPLE 1

Preliminary preparation of methylmagnesium chloride

A solution of methylmagnesium chloride for use in Examples 3 to 7 was prepared as follows:

Gaseous methyl chloride was slowly bubbled through a stirred suspension of magnesium turnings (3.0 g, 0.12 moles) in tetrahydrofuran (250 ml). Reaction between the methyl chloride and magnesium was initiated using a few mg of iodine. The rate of addition of methyl chloride was such that the reaction mixture boiled under reflux without external heating. Addition of methyl chloride was stopped when all the magnesium had been consumed. The reaction mixture contained excess methyl chloride at this stage.

EXAMPLE 2

Preliminary preparation of methylmagnesium iodide

A solution of methylmagnesium iodide for use in Examples 11 and 12 was prepared as follows:

Methyl iodide (40 ml, 0.64 moles) was added dropwise to a stirred suspension of magnesium turnings (8.0 g, 0.33 moles) in diethyl ether (400 ml). The rate of addition of methyl iodide was such that the reaction mixture boiled under reflux without external heating. Addition of methyl iodide was stopped when all the magnesium had been consumed. The reaction mixture contained excess methyl iodide at this stage.

EXAMPLE 3

Electrolytic preparation of a trimethylindium tetrahydrofuran (thf) adduct using excess methyl chloride A solution of tetrahydrofuran in the methylmagnesium chloride containing excess methyl chloride prepared as described in Example 1 was electrolysed using a Pt cathode (1×1 cm plate) and a sacrificial indium wire anode at room temperature (about 20° C.). Applied voltages of between 20–50 V gave currents of between 120–150 mA. The reaction was continued until 5.66 g of indium wire had been consumed. There was no metal deposited at the cathode.

The mixture was filtered and the thf was removed in vacuo. The pure liquid product was separated from residual methyl magnesium chloride by condensing it into a $-196°$ C. trap *in vacuo*, whilst the distillation vessel was heated to a temperature of between 60° and 100° C. (Yield=55% to 79%.)

The product was investigated using:

(i) $^1$H nuclear magnetic resonance (nmr) spectra recorded on a PE R12B (Trade Mark) instrument at 60 MHz.

(ii) Infrared absorption spectra recorded on a PE 577 (Trade Mark) instrument using thin films on nujol mulls between caesium iodide plates; and (iii) Mass spectra measured on a VG Micromass 12 (Trade Mark) mass spectrometer.

The results obtained are given in Tables 1 to 3 below.

TABLE 1

$^1$H NMR Data for the product of Example 3

$\delta$ ($^1$H)(neat liquid)

4.2(4H, t, C$\underline{H}_2$CH$_2$CH$_2$CH$_2$O)2.3(4H, m,

CH$_2$C$\underline{H}_2$C$\underline{H}_2$CH$_2$O)O, O(9H, s, In(CH$_3$)$_3$)

All values relative to external TMS (tetra methyl silane).
Abbreviation:
s = singlet,
t = triplet,
m = multiplet

TABLE 2

Infrared absorption spectrum
for the product of Example 3 ir max: cm$^{-1}$
2960 vs, 2910 vs, 2880 vs, 2840 vs(sh), 2270 vw, 1460 m
1365 w, 1340 vw, 1290 vw, 1245 vw, 1180 w, 1150 m, 1070 s(sh)
1050 vs(sh), 1040 vs, 915 m, 880 s, 840 w(sh), 680 vs(br)
670 s (br) 515 vw(sh), 485 vs.

Abbreviations used in TABLE 2:
vw = very weak, w = weak, m = medium, s = strong, vs = very strong, sh = shoulder, br = broad, ir = infrared, max = absorption maxima.

TABLE 3

Mass spectrum
for the product of Example 3 m/e (solid probe): 71 [C$_4$H$_7$O]$^+$ 72 [C$_4$H$_8$O]$^+$ 115 [In]$^+$
130 [MeIn] 145 [Me$_2$In]$^+$ 160 [Me$_3$In]$^+$ (s = 70° C., I = 15 eV)

Abbreviations s = source temperature, I = ionisation energy, m/e = mass:charge ratio (assignment).

EXAMPLE 4

Electrolytic preparation of a trimethylindium tetrahydrofuran (thf) adduct in the absence of excess alkyl halide Solid methylmagnesium chloride (3.0 g), prepared by evaporating a solution prepared as in Example 1 to dryness, was dissolved in thf (100 ml) and the mixture was electrolysed as described in Example 3. An applied voltage of 50 V gave a maximum current of 60 mA. During the course of the reaction magnesium was deposited at the cathode and 2.0 g of indium wire were consumed.

The pure liquid product In(CH$_3$)$_3$.thf was obtained as described in Example 3.

EXAMPLE 5

Electrolytic preparation of a trimethylgallium thf adduct

A procedure similar to that described in Example 3 was used except that the indium anode used in Example 3 was replaced by a gallium pool anode heated to a temperature of 70° C. The mixture was stirred continuously throughout the reaction.

Initially an applied voltage of 40 V gave a current of 25 mA. The reaction was continued for 24 hours during which time the current had risen to 140 mA at an applied voltage of 20 V. The liquid product Me$_3$Ga(thf) was obtained using a procedure similar to that described in Example 3. The product of Example 5 was investigated using:

(i) $^1$H nuclear magnetic resonance (nmr) spectra recorded on a PE R12B (Trade Mark) instrument at 60 MHz;
(ii) Infrared absorption spectra recorded on a PE 577 (Trade Mark) instrument using a thin film between CsI plates;
(iii) Mass spectra measured on a VG Micromass 12 (Trade Mark) mass spectrometer.

The results obtained are listed in Tables 4 to 6 respectively as follows:

TABLE 4

$^1$H nmr spectrum for the product of Example 5

δ ($^1$H) in d$^6$ benzene:

3.6(t, 4H, C$\underline{H_2}$CH$_2$CH$_2$C$\underline{H_2}$O)

TABLE 4-continued $^1$H nmr spectrum for the product of Example 5

1.6(m, 4H, CH$_2$C$\underline{H_2}$C$\underline{H_2}$CH$_2$O)

−0.3(s, 9H, Ga(C$\underline{H_3}$)$_3$)

(δ values relative to methine protons of benzene at 7.3δ).
Abbreviations:
s = singlet;
t = triplet;
m = multiplet.

TABLE 5

Infrared absorption spectrum
for the product of Example 5 ir max: cm$^{-1}$ (thin film:)
2980 m, 2940 s, 2890 m, 1450 w, 1365 vw, 1340 vw,
1250 vw(br), 1190 m, 1060 w(br,sh), 1030 s, 915 w, 875 m,
740 s(sh), 720 s, 670 w, 580 vw(sh), 550 vs, 515 vw Abbreviations:
vw = very weak, w = weak, m = medium, s = strong, vs = very strong, br = broad, sh = shoulder, ir = infrared, max = absorption maxima.

TABLE 6

Mass spectrum for
the product of Example 5 m/e (batch inlet):
69/71 [Ga]$^+$ 71 [C$_4$H$_7$O]$^+$ 72 [C$_4$H$_8$O]$^+$
84/86 [MeGa]$^+$ 99/101 [Me$_2$Ga]$^+$ 114/116 [Me$_3$Ga]$^+$
141/143 [Ga.thf]$^+$ 171/173 [Me$_2$Ga.thf]$^+$ (s = 90° C., I = 15 eV)

Abbreviations:
s = source temperature, I = ionisation energy, m/e = mass:charge ratio (assignment).

EXAMPLE 6

Electrolytic preparation of a triethylindium thf adduct

A procedure similar to that described in Example 3 was followed except that ethylmagnesium chloride in excess ethyl chloride was used instead of the methylmagnesium chloride in excess methyl chloride used in Example 3.

EXAMPLE 7

Electrolytic preparation of a triethylgallium thf adduct

A procedure similar to that described in Example 6 was used except that the indium anode used in Example 6 was replaced by a gallium pool anode heated to a temperature of 70° C.

The products of Examples 3 to 7, which may be regarded as intermediate or precursor adducts, may be used to produce, by the method of copending UK Patent Application No. 8233121, further adducts, which may be regarded as final adducts, suitable for conversion into compound semiconductors. The following Examples 8 to 10 illustrate conversion into the final adducts.

EXAMPLE 8

Preparation of a trimethylindium-triethylamine adduct

Triethylamine (20 ml) was added to the adduct (CH$_3$)$_3$In.thf prepared electrolytically as described in Example 3, the mixture was stirred at room temperature for 30 minutes and the triethylamine was then removed in vacuo to leave a colourless crystalline solid which was purified by sublimation (60°–110° C.) in vacuo into a cold trap at a temperature of about −196° C. The product Me₃In.NEt₃ had a melting point of 94°–96° C.

The product of Example 8 was investigated using:
(i) microanalysis
(ii) $^1$H nuclear magnetic resonance (nmr) spectra recorded on a PE R12 (Trade Mark) instrument at 60 MHz;
(iii) infrared absorption spectra recorded on a PE 577 (Trade Mark) instrument using nujol mulls between plates; and (iv) mass spectra measured on a VG Micromass 12 (Trade Mark) mass spectrometer.

The results obtained are listed in Tables 7 to 10 respectively as follows.

TABLE 7

Microanalysis data for the product of Example 8

C₉H₂₄InN calculated: C, 41.4;  H, 9.1;  N, 5.4;  In 44.1
          found:      C, 41.1;  H, 9.0;  N, 5.2;  In 44.6

TABLE 8

H nmr spectra for the product of Example 8

δ($^1$H in d$^8$ toluene: 2.3(6H,q,N(CH₂CH₃)₃)0.9(9H,t,N(CH₂CH₃)₃)
−0.1(9H,s,In(CH₃)) (δ values rel. to methine proton of toluene at 7.2δ).

Abbreviations:
s = singlet, t = triplet, q = quartet.

TABLE 9

Infrared absorption spectra for the product of Example 8

ν (cm$^{-1}$) "Nujol Mull":
2280 vw; 1330 vw; 1320 vw; 1290 w; 1190 m; 1170 s; 1150 s;
1090 m; 1055 m; 1025 w; 1005 w; 900 vw(br); 800 vw; 790 vw;
730 m; 680 w; 620 w(br,sh); 550 w; 475 vs; 455 m(sh);
475 vs; 455 m(sh); 420 vw.

Abbreviations:
vw = very weak, w = weak, m = medium, sh = shoulder, s = strong, vs = very strong.

TABLE 10

Mass spectrum for the product of Example 8 m/e (Solid probe.) (Source temperature = 170° C. Ionisation energy = 30 eV.)
86 [C₅H₁₂N[⁺ 115 [In]⁺ 130 [InMe]⁺ 101 [C₆H₁₅N]⁺ 145 [InMe₂]⁺

The data in Tables 7 to 10 confirms the structure of the adduct formed, i.e. (CH₃)₃In.N(C₂H₅)₃.

EXAMPLE 9

Preparation of a trimethylindium-trimethylphosphine adduct

A similar procedure to that used in Example 8 was follows but using the adduct (CH₃)₃In.(thf) and P(CH₃)₃ (10 g) as starting materials.

The product of Example 9 which was found to have a melting point of 43°–45° C. was investigated using:
(i) composition microanalysis; the results are given in Table 11 as follows:
(ii) $^1$H nmr spectra recorded as for the product of Example 7 and the results obtained are given in Table 12 as follows.
(iii) Infrared absorption spectra recorded as for the product of Example 7 and the results obtained are given in Table 13, as follows; and
(iv) Mass spectra recorded as for the product of Example 7 and the results obtained are given in Table 14 as follows.

TABLE 11

Microanalytical results for the product Example 9

Results found:      C: (30.46%);  H: (7.89%);  In (49.6%)
Figures calculated: C: (30.50%);  H: (7.63%);  In (48.9%)

TABLE 12

$^1$H nmr spectrum for the product of Example 8

δ($^1$H) in d$^8$ -toluene: 0.8(d, 9H, P(CH₃)₃),
−0.1(s,9H,In(CH₃)₃)

TABLE 13:

Infrared absorption spectrum for the product of Example 9 ir max cm$^{-1}$ "Nujol" Mull:
2250 vw; 1300 w; 1280 m; 1160 vw; 1140 m; 950 vs;
940 vs; 850 vw; 840 vw; 735 vs; 720 s; 680 vs; 630 w(br,sh);
520 vw; 482 vs; 470 m(sh);

TABLE 14

Mass spectrum for the product of Example 9 m/e (solid probe):
61 [C₂H₆P]⁺ 76 [C₃H₉P]⁺ 115 [In]⁺ 130 [MeIn]⁺
145 [Me₂In]⁺ 160 [Me₃In]⁺ (s = 100° C., I = 30 eV)

Abbreviations;
s = source temperature, I = ionisation energy

EXAMPLE 10

Preparation of a trimethylindium-triethylphosphine adduct

A similar procedure to that used in Example 8 was followed but using the adduct (CH₃)₃In.thf and P(C₂H₅)₃ (5 g) as starting materials.

The product (melting point 33°–36° C.) of Example 10 was investigated using:
(i) Composition microanalysis;
(ii) $^1$H nmr spectra;
(iii) Infrared absorption spectra;
(iv) Mass spectra;
in the same way as in previous Examples.

The results obtained are given in Tables 15 to 18 respectively as follows.

TABLE 15

Microanalytical results for the product of Example 10

Results found:      C (39.2%); H (9.1%); P (10.1%); In (42.0%)
Figures calculated: C (38.8%); H (8.6%); P (11.1%); In (41.5%)

TABLE 16

$^1$H nmr spectrum for the product of Example 10

δ ($^1$H) in d$^6$ benzene:
1.1, 0.75(m,15H, P(C₂H₅)₃)

TABLE 16-continued 0.0(s,9H,In(CH$_3$)$_3$)

TABLE 17

Infrared absorption spectrum
for the product of Example 10 ir max cm$^{-1}$ "Nujol Mull"

2270 w; 1300 w; 1250 m; 1170 w(sh); 1145 m; 1040 s;
1010 w; 970 w; 860 vw; 770 s; 750 s 730 s(sh); 720 s(sh);
680 vs(br); 630 w(sh); 520 vw(sh); 475 vs; 460 s(sh).

TABLE 18

Mass spectrum
for the product of Example 10 m/e (solid probe):
61[C$_2$H$_6$P]$^+$ 62[C$_2$H$_7$P]$^+$ 75[C$_3$H$_8$P]$^+$ 90[C$_4$H$_{11}$P]$^+$
103[C$_5$H$_{12}$P]$^+$ 115[In]$^+$ 118[C$_6$H$_{15}$P]$^+$ 130[MeIn]$^+$
145[Me$_2$In]$^+$ 160[Me$_3$In]$^+$ 233[In.PEt$_3$]$^+$
263[Me$_2$In.PEt$_3$]$^+$ (s = 50° C., I = 25 eV.)

Abbreviations:
s = source temperature, I = ionisation energy, m/e = mass to charge ratio.

EXAMPLE 11

Electrolytic preparation of a trimethyl gallium diethyl ether adduct

The diethyl ether solution of methylmagnesium iodide containing excess methyl iodide prepared as described in Example 2 was electrolysed using a Pt Cathode (1×1 cm plate) and a sacrificial gallium pool anode (about 20–40 g). The mixture was heated to 50°–60° C. (using a wax bath) and was stirred continuously throughout the reaction. An applied voltage of 100 volts gave a current of 30 mA which rose to 70 mA during the course of the reaction. The reaction was allowed to proceed for 72 hours after which time the reaction mixture was allowed to cool. About 3 g of Ga had dissolved. After filtration the diethyl ether was removed *in vacuo*. The pure liquid product was separated from residual methylmagnesium iodide by vacuum distillation (60° C.) into a cold trap at about −196° C. The product (measured boiling point 98.3° C. corresponding to the published value) was investigated in the same manner as in above Examples using $^1$H nmr spectra mass spectra data and infrared absorption spectra. The results are given in Tables 19 to 21 respectively as follows:

TABLE 19

$^1$H nmr data
for the product of Example 10

δ($^1$H) (neat liquid): −0.2(s,9H,Ga(CH$_3$)$_3$),
1.4(t,6H,(CH$_3$CH$_2$)$_2$O) 3.95 (q,4H,(CH$_3$CH$_2$)$_2$O)

Abbreviations:
s = singlet, t = triplet, q = quartet

TABLE 20

Mass spectral data for
the product of Example 11 (batch inlet):

m/e (assignment):
69/71 [Ga]$^+$ 74 [Et$_2$O]$^+$ 84/86 [MeGa]$^+$
99/101 [Me$_2$Ga]$^+$ 114/116 [Me$_3$Ga] s = 140° C., I = 30 eV (s = source temperature, I = ionisation energy)

TABLE 21

Infrared spectral data
for the product of Example 11 ir max: cm$^{-1}$
2940 vs(br), 2860 s(sh), 1450 m, 1380 m, 1350 w(sh),
1290 vw, 1260 vw, 1210 s, 1150 m, 1115 m, 1090 m, 1020 s(br),
900 vw, 720 vs(br), 580 vs(br), 520 vs(br), 380 vw(br),
320 vw(br). (Thin Film)

Abbreviations:
vw = very weak, w = weak, m = medium, s = strong, vs = very strong, sh = shoulder, br = broad.

The data given in Tables 19 to 21 confirms that the product of Example 10 is the Me$_3$Ga.OEt$_2$ adduct.

As noted above, the route described in Example 11 is superior to previously used methods for the preparation of Me$_3$Ga.OEt$_2$ in that previous methods have involved the prior synthesis of GaCl$_3$ prior to alkylation by the Grignard reagent.

The adduct Me$_3$Ga.OEt$_2$ can be converted into Me$_3$GaQ (Q=NEt$_3$, PMe$_3$ or PEt$_3$) by methods similar to those of Examples 8 to 10 above.

EXAMPLE 12

Electrolytic preparation of a trimethylindium diethyl ether adduct

The diethyl ether solution of methylmagnesium iodide containing excess methyl iodide prepared as described in Example 2 was electrolysed using a Pt cathode (1×1 cm plate) and a sacrificial indium wire anode at room temperature (about 20° C.). Applied voltages of between 60 V and 100 V gave a current of between 10–20 mA. The reaction was continued until 3.75 g of indium wire had been consumed (about 100 hr). During the course of the electrolysis a small amount of metal was deposited at the cathode.

The mixture was filtered and the diethyl ether was removed in vacuo. The pure liquid product was separated from residual methylmagnesium iodide by condensing it into a −196° C. trap in vacuo, whilst the distillation vessel was heated at a temperature of about 100° C.

The product was investigated using $^1$H nuclear magnetic resonance (nmr) spectra and infrared spectra in the same manner as for previous Examples.

The results are listed in Tables 22 and 24 below.

TABLE 22

$^1$H nmr data
for the product of Example 12

δ($^1$H) (neat liquid):
0.0(s,9H,In(CH$_3$)$_3$) 1.6(t,6H,(CH$_3$CH$_2$)$_2$O)
4.1(q,4H,(CH$_3$CH$_2$)$_2$O)

All values relative to external TMS (tetramethylsilane)

TABLE 24

Infrared (ir) data
for the product of Example 12 ir max. cm$^{-1}$:
2980 vs, 2900 vs, 2840 vs, 2280 w, 1480 m(sh), 1465 s,
1445 s, 1385 vs, 1350 w, 1320 w(sh), 1300 m(sh), 1290 m, 1190 s,
1150 vs, 1120 s, 1090 vs, 1050 vs, 1010 s(sh), 1000 s, 905 m,
830 m, 780 s, 680 vs(br), 625 m(sh), 480 vs, 410 w. (Thin Film)

The above data confirms that the product of Example 12 was Me$_3$In.OEt$_2$ adduct.

The precursor adducts prepared in Examples 11 and 12 may be converted into final adducts (for use in semiconductor production) in the same way as described in

EXAMPLE 8 to 10 above. The following Example 13 illustrates such a conversion.

EXAMPLE 13

Preparation of trimethylindium triethylamine adduct

Triethylamine (5 ml) was added to the adduct $(CH_3)_3In.OEt_2$ prepared electrolytically as described in Example 12. The mixture was stirred at room temperature for 30 minutes and the triethylamine was removed in vacuo to leave a colourless crystalline solid which was purified by sublimation (60°–110° C.) in vacuo into a cold trap at about $-196°$ C.

The product of Example 13 was found to have spectral ($^1$H nmr, infrared) characteristics identical with a sample of $(CH_3)_3In.NEt_3$ prepared as described in Example 8 above.

EXAMPLE 14

Electrolytic preparation of trimethylgallium di-isopentyl ether adduct

A $CH_3MgI$ solution was prepared as in Example 11 but using di-isopentyl ether (100 ml) instead of diethyl ether.

The solution was electrolysed using a Pt cathode (1×1 cm plate) and a sacrificial gallium pool anode (110 g). The mixture was heated to 80° C. and was stirred continuously throughout the reaction. A voltage of 200 V was applied and initially gave a current of 6 mA. The reaction was allowed to proceed for approximately 72 hours. During the reaction the current rose to 100 M. Magnesium was deposited at the cathode during the electrolysis. During the latter stages of the electrolysis a fine precipitate appeared in reaction mixture. The mixture was decanted. All volatiles were distilled into a $-196°$ C. trap in vacuo whilst the distillation vessel was heated. Excess ether was removed in vacuo. Adduct formation was confirmed by nmr, by a continued improvement of integral ratios during removal of excess ether.

EXAMPLE 15

Electrolytic preparation of trimethylgallium di-n-butyl ether adduct

A $CH_3MgI$ solution was prepared as in Example 2 but in di-n-butyl ether (150 ml) instead of diethyl ether. The solution was electrolysed using a Pt cathode and sacrificial gallium pool anode. A voltage of 160 V was applied and gave a current of 2.5 mA. The reaction was allowed to proceed for 100 hours. The mixture was filtered and excess ether was removed in vacuo. The liquid product was obtained by condensing it into a $-196°$ C. trap in vacuo whilst the distillation vessel was heated. Excess ether was again removed in vacuo. The formation of the adduct was confirmed by nmr.

EXAMPLE 16

Electrolytic preparation of trimethylgallium diphenyl ether adduct

This adduct was prepared in a manner analogous to Example 14 above using diphenyl ether as the solvent for the electrolysis.

EXAMPLE 17

Electrolytic preparation of trimethylgallium anisole adduct

This adduct was prepared in a manner analogous to Example 14 using anisole as the solvent for the electrolysis (the volume of anisole being in greater excess than the corresponding di-isopentyl ether in Example 14).

Although, as noted above, it may be desirable to convert the intermediate adducts into the final adducts for use in semiconductor compound production, the radical-free metal trialkyls may nevertheless be produced from the intermediate adducts if required, e.g. as in the following Example.

EXAMPLE 18

Conversion of trimethylgallium diethyl ether adduct into radical free trimethylgallium This conversion involves use of the method described in UK Patent Application No. 8218820.

Di-isopentyl ether (20 ml, 97 mmol) was added to the product of Example 11 (2 g, 10 mmol) at ambient temperature (20° C.). A radical exchange reaction took place between the di-isopentyl ether and the diethyl ether radical contained in the adduct. The diethyl ether evolved was removed in vacuo at ambient temperature. Proton nmr data indicated complete displacement of the diethyl ether.

The resulting solution was heated to 190° C. using an oil bath and this temperature was maintained for about 0.5 hr. The pure trimethylgallium (boiling point 55°–56° C.) produced by the dissociation of the trimethylgallium di-isopentyl ether adduct at this temperature was readily separated and collected by fractional distillation at atmospheric pressure through a column (22 cm long and 1.5 cm in diameter) packed with Fenske helices or glass beads.

Confirmation of the product was obtained by mass spectrum and nmr measurements and these are given in Tables 25 and 26 respectively as follows.

TABLE 25

$^1$H nmr data for the product of Example 18

$\delta(^1H)$ in benzene: 0.0(s, $Ga(CH_3)_3$)
(using as reference methine protons in benzene).

TABLE 26

Mass spectral data for the product of Example 18 m/e (assignment): 69/71 [Ga]$^+$ 84/86 [MeGa]$^+$
99/101 [Me$_2$Ga]$^+$ 114/116 [Me$_3$Ga]$^+$
(s = 110° C., I = 15 eV)

s = source temperature, I = ionisation energy.

The above data confirms that the product of Example 18 is trimethylgallium, Me$_3$Ga.

The pure trimethylgallium produced as in Example 18 may be used in the production of gallium compound semiconductors by known vapour phase epitaxy methods, e.g. by reaction with AsH$_3$.

EXAMPLE 19

Preparation of radical-free trimethylgallium from the adduct produced in Example 14

The product of Example 14 was fractionally distilled by heating by an oil bath at a bath temperature of 100°

C. and distilling through a column as in Example 18 to remove excess methyl iodide (until no further methyl iodide distilled over).

Pure trimethyl gallium was then collected by heating at a bath temperature of 190° C. for several hours. Since the boiling point of the trimethyl gallium is much less than that of the di-isoputyl ether (boiling point 160° C.) the former was readily separated from the latter in the fractionating column.

The trimethyl gallium product was checked by mass spectrometry.

EXAMPLE 20

Preparation of radical-free trimethylgallium from the adduct produced in Example 17

Most of the unreacted methyl iodide (boiling point 42° C.) was removed from the product of Example 17 by distillation at an oil bath temperature of 100° C. More anisole (100 cm$^3$) was added to the product and the suspension heated to an oil bath temperature of 150° C. Trimethylgallium (boiling point 56° C.) was distilled through a fractionating column and was collected. Mass spectroscopic studies showed contamination by methyl iodide.

Crude trimethylgallium produced by this method was then slowly added to anisole (250 cm$^3$). Volatile impurities were removed by pumping (evacuation) at room temperature (20° C.) and then again at an oil bath temperature of 60° C. The mixture was heated to an oil bath temperature of 150° C. whereupon pure trimethylgallium (boiling point 56° C.) distilled through the fractionating column and was collected. Mass spectroscopic studies confirmed purification of the trimethylgallium.

EXAMPLE 21

Preparation of radical-free trimethylgallium from the adduct produced in Example 16

An analogous procedure to Example 19 was followed using diphenyl ether instead of the anisole. In this case the distillation temperature (of the oil bath) was 140° C. at which bath temperature the trimethylgallium was collected by fractionation.

EXAMPLE 22

Preparation of radical-free trimethyl indium from the adduct produced in Example 12

The product of Example 12 was converted into radical-free trimethyl indium by the addition of benzene followed by distillation in the manner described by E Todt and R Dotzer in Z Anorg Chem 1963, 321, 120.

The final adducts prepared by radical exchange from intermediate adducts e.g. as in Examples 3 to 7 and 11, 12, 14 and 15 may be converted into compound semi-conductors in a known way.

For example, the products of Examples 8 and 9 may be pyrolytically decomposed in the manner described by H. Renz and J. Weidlein in Electronics Letters, Volume 16, Mar. 13, 1980, No 6, Page 228.

Alternatively, a hydride of the Group V element, e.g. PH$_3$, may be reacted with the final adduct as in the method described in the article "A new approach to MOCVD of indium phosphide and gallium-indium arsenide" by R. H. Moss and J. S. Evans in J. Crystal Growth, Vol 55 (1981) Page 129.

The adducts produced in examples 8 and 9 themselves be converted into the compound semiconductors InN or InP by decomposition, e.g. in the presence of NH$_3$ or PH$_3$.

Radical-free trialkyls of gallium and indium (e.g. as produced in Examples 18 to 22) may be converted into compound semi-conductors by known methods. For example, radical-free trialkyls of indium have previously been pyrolytically decomposed in the presence of a Group V hydride to give InP, InAs and InSb as described in the following references:

(i) the article by: R. Didchenko, J. E. Alix and R. H. Toeniskoetter, in J. Inorg. Nucl. Chem., 1960, 14, 35;

(ii) the article by: H. M. Manasevit and W. I. Simpson, in J. Electrochem. Soc., 1973, 120, 135;

(iii) the article by: B. Harrison and E. H. Tompkins, in Inorg. Chem. 1962, 1, 951.

DESCRIPTIVE EXAMPLE A

The homogeneous alloy Ga$_2$Mg$_5$ was first obtained in a pure form by melting together and mixing stoichiometric quantities of gallium and magnesium in a sealed, induction heated graphite tube located in a sealed silica tube.

Dry methyl iodide (62.5 ml, 1 mole) was then added slowly, with stirring, to a suspension of finely ground sample of the Ga$_2$Mg$_5$ alloy (0.3 molar in Ga) in dry di-isopentyl ether. The reaction was conducted in a nitrogen atmosphere, and about 2 mg of iodine was added to initiate the reaction. The reaction is exothermic and the rate of addition of methyl iodide was such that the mixture remained very hot without external heating. During the course of the addition of methyl iodide the initially dark mixture lightened considerably as magnesium iodide was deposited. After all the methyl iodide had been added the flask containing the mixture was heated externally by a paraffin wax bath located on a hot plate at a bath temperature of between 80° 0 and 90° 0 for about 2 hr. with stirring until, upon complete reaction, the reaction mixture became pure white. Most unreacted methyl iodide was removed by adding fresh magnesium powder and further heating the mixture at 60° 0 for 1 hr.

The mixture was then fractionally distilled by heating at a bath temperature of about 100° C. and distilling through a 22 cm long × 1.5 cm diameter column packed with Fenske helices. The first fraction collected by heating at this moderate temperature was a small quantity of methyl iodide (boiling point 41°-43° C.). This fraction was readily separated. The distillation was continued at this temperature until the vapour pressure of unreacted methyl iodide fell and no further methyl iodide distilled over.

Pure trimethyl gallium (boiling point 55°-56° C.) was then collected by heating the mixture at a bath temperature of about 190° C. for about 6 hr. This temperature is above the decomposition temperature of the adduct formed.

Since the boiling point of the trimethyl gallium is much less than that of the di-isopentyl ether (boiling point 160° C.) the former was readily separated and collected in the fractionated column when the two dissociated from the adduct by heating at 190° C.

None of the trimethyl gallium fraction collected had to be discarded. All was useful material.

The trimethyl gallium product was checked by mass spectrometry and found to be relatively pure.

EXAMPLE B

Impure Me$_3$Ga (0.17 moles) was added with stirring to a large excess of di-isopentyl ether (0.98 moles). When the exothermic reaction had subsided the mixture was stirred at room temperature for 12 hr. The Me$_3$Ga-dpe adduct so formed was then fractionally distilled as in Descriptive Example A.

In another experiment not forming part of the present invention but carried out for purposes of comparison when trimethyl gallium contaminated with methyl iodide but in the absence of di-isopentyl ether in the form of an adduct was heated trimethyl gallium required only moderate external heating (90°–100° C.) for distillation. However, great difficulty was experienced in removing the methyl iodide. This showed that the adduct formation (as in Examples 1 and 2) is necessary in order to remove the methyl iodide. The methyl iodide may in fact be removed from the trimethyl gallium by carrying out the procedure of Example 2.

The formation and then fractional distillation of a trimethyl gallium di-isopentyl ether adduct can also facilitate the removal of impurities other than methyl iodide. For example, impurities such as the volatile alkyls of Group II and Group IV elements are removed in the fractional distillation process at much lower temperatures than the temperature (180° C.) required for distillation of the trimethyl gallium.

We claim:

1. A method of a producing compound semiconductor materials comprising producing an adduct of an organometallic compound M(R$^1$)$_3$, where M is either indium or gallium and R$^1$ is either methyl or ethyl, and where the adduct is of formula M(R$^1$)$_3$. L, by the steps of:
   (i) electrolysing, using a sacrificial anode of the metal M, a solution containing components 1 and 2 as follows:
      component 1: one or more organomagnesium halide compounds R$^1$MgX where X is a halide radical selected from Cl, Br and I and where R$^1$ is as defined above;
      component 2: a polar aprotic liquid which is a solvent for component 1, which provides the source of the radical L, and which is selected from the group consisting of tetrahydrofuran, diethyl either, di-n-propyl ether, di-n-butyl ether, di-n-pentyl ether, di-isopentyl ether, di-phenyl ether, and alkyl phenyl ethers having from 1 to 7 carbon atoms in the alkyl group; and
   (ii) converting the adduct M(R$^1$)$_3$. L formed by the electrolysis into a further product from which a semiconductor compound may be obtained.

2. A method as claimed in claim 1 and which comprises, prior to the electrolysis, the step of producing the compound R$^1$MgX by addition of excess of the compound R$^1$X to a suspension of magnesium in an ethereal solvent.

3. A method as claimed in claim 1 and wherein the concentration of component 1 in component 2 is between 0.01 and 5 mole/liter.

4. A method as in claim 1 wherein step (ii) is practiced utilizing a radical exchange reaction with a further less volatile solvent to form an adduct with said further solvent.

5. A method as in claim 4 further comprising the step of decomposing the further product obtained in step (ii) to form said semiconductor compound.

6. A method as in claim 1 wherein step (ii) is practiced utilizing a radical exchange reaction with a Group V containing species to form an adduct with said Group V containing species.

7. A method as in claim 6 further comprising the step of decomposing the further product obtained in step (ii) to form said semiconductor compound.

8. A method as in claim 1 wherein step (ii) is practiced by distilling the solution above the adduct decomposition temperature to separate the organometallic compound M(R$^1$)$_3$ from the radical provided by the polar aprotic liquid, component 2.

9. A method as in claim 8 further comprising the step of decomposing the further product obtained in step (ii) to form said semiconductor compound.

10. A method as claimed in claim 8 and wherein M(R$^1$)$_3$ is trimethyl indium and the distillation follows the addition of benzene to the adduct.

11. A method as claimed in claim 8 and wherein M(R$^1$)$_3$ is trimethylgallium and the distillation is at a temperature above the adduct dissociation temperature, the trimethylgallium being collected by fractionation.

12. A method as claimed in claim 1 and wherein the solution electrolysed additionally contains a third component, component 3, which is one or more organic halides R$^1$X$_A$ where R$^1$ is as defined in claim 1 and X$_A$ is a halid radical, the polar aprotic liquid being a solvent also for component 3.

13. A method as claimed in claim 12 and wherein X$_A$ is the same as X.

* * * * *